United States Patent
Chou et al.

(10) Patent No.: US 10,376,866 B2
(45) Date of Patent: Aug. 13, 2019

(54) METHOD OF REGENERATION OF A SPENT SULFURIC ACID CATALYST FROM ALKYLATION OF OLEFINS AND ALKANES VIA PAIRED OXIDATION

(71) Applicants: Chao-Shan Chou, Tainan (TW); Tse-Chuan Chou, Tainan (TW)

(72) Inventors: Chao-Shan Chou, Tainan (TW); Tse-Chuan Chou, Tainan (TW)

(*) Notice: Subject to any disclaimer, the term of this patent is extended or adjusted under 35 U.S.C. 154(b) by 73 days.

(21) Appl. No.: 15/633,846

(22) Filed: Jun. 27, 2017

(65) Prior Publication Data

US 2018/0369792 A1    Dec. 27, 2018

(51) Int. Cl.
*B01J 27/30* (2006.01)
*B01J 38/12* (2006.01)
*C07C 2/62* (2006.01)

(52) U.S. Cl.
CPC .............. *B01J 27/30* (2013.01); *B01J 38/12* (2013.01); *C07C 2/62* (2013.01); *C07C 2527/054* (2013.01)

(58) Field of Classification Search
CPC ....... B01J 27/30; B01J 38/12; C07C 2527/02; C07C 2527/054
See application file for complete search history.

(56) References Cited

U.S. PATENT DOCUMENTS

| | | | | |
|---|---|---|---|---|
| 5,523,518 A * | 6/1996 | Shikami | ..................... | C25B 1/22 204/174 |
| 5,547,655 A * | 8/1996 | Chou | ....................... | C01B 17/92 204/157.15 |
| 5,888,920 A * | 3/1999 | Chou | ....................... | B01J 27/30 208/13 |
| 2013/0334059 A1* | 12/2013 | Domon | ................... | C25B 11/12 205/554 |
| 2014/0072836 A1* | 3/2014 | Mills | ........................ | C25B 1/04 429/8 |
| 2016/0168732 A1* | 6/2016 | Swiegers | ................ | C25B 15/02 429/500 |

OTHER PUBLICATIONS

Southern State Chemicals, Chemical Plant Control data book, published 1976.*

* cited by examiner

*Primary Examiner* — Jun Li
(74) *Attorney, Agent, or Firm* — Bacon & Thomas, PLLC

(57) ABSTRACT

A spent sulfuric acid catalyst from an alkylation unit is regenerated via a paired oxidation electrolysis, wherein active intermediates are generated via both anodic oxidation and cathodic reduction without adding an additional organic peroxide during the electrolysis. The organic impurities in the spent sulfuric acid catalyst are decomposed by the active intermediates, and removed therefrom via evaporation.

11 Claims, 2 Drawing Sheets

US 10,376,866 B2

METHOD OF REGENERATION OF A SPENT SULFURIC ACID CATALYST FROM ALKYLATION OF OLEFINS AND ALKANES VIA PAIRED OXIDATION

FIELD OF THE INVENTION

The present invention is related to a method of regeneration of a spent sulfuric acid catalyst from alkylation of olefins and alkanes via a paired oxidation electrolysis.

BACKGROUND OF THE INVENTION

In U.S. Pat. No. 5,547,655, the inventors of the present invention disclose an electrochemical process for recovery and regeneration of sulfuric acid from the spent sulfuric acid catalyst of the alkylation of C3-C5 olefins and alkanes by using active intermediates generated by electrolysis, heat and photolysis. Both the organic impurities and water containing in the spent sulfuric acid catalyst are simultaneously removed under mild operating conditions. Over 90% water and 95% organic impurities of its initial value, respectively, are efficiently removed from the spent sulfuric acid catalyst, which avoids the disadvantages of the combustion of the corrosive spent sulfuric acid catalyst at high temperature, the purification and oxidation of $SO_2$ at high temperature in the traditionally commercialized process.

In U.S. Pat. No. 5,547,655, preferably an oxidant such as an organic peroxide is introduced into the spent sulfuric acid catalyst to generate active intermediates from the surface of the anode during electrolysis. That is the active intermediates are generated substantively via anodic oxidation.

SUMMARY OF THE INVENTION

A primary objective of the present invention is to provide an improvement to the electrochemical process disclosed in U.S. Pat. No. 5,547,655 via a paired oxidation, wherein active intermediates are generated via both anodic oxidation and cathodic reduction without adding an additional organic peroxide during electrolysis. The term "paired oxidation" used in the present invention means oxidants (active intermediates) are generated both at the anode and the cathode, and oxidation reactions of the organic impurities by the oxidants (active intermediates) undergo thereafter.

The present invention uses an $O_2$-diffusion cathode, wherein air or $O_2$-containing gas is introduced into said spent sulfuric acid catalyst through the $O_2$-diffusion cathode, so that oxidation reactions also occur at the $O_2$-diffusion cathode, forming oxidants for examples hydrogen peroxide, hydroxyl free radicals and sulfate anion free radicals, and thus the organic impurities are decomposed via reactions with oxygen contained in air or the $O_2$-containing gas, water contained in the spent sulfuric acid catalyst, and the so-formed oxidants.

In this invention, the sources for forming the oxidants (active intermediates) in the paired oxidation are water and air or oxygen-containing gas. The active intermediates such as hydrogen peroxide, persulfate anion, sulfate anion, free radical, hydroxyl free radicals are generated electrochemically or photoelectrochemically by using electricity energy and photo energy and heat as energy source. The amount of sulfuric acid species in the spent sulfuric acid catalyst, usually over 90 wt %, is substantially not changed while the organic impurities, ca 2-7 wt %, and water, ca 2-8 wt %, are removed according to the method of the present invention, so that the spent sulfuric acid catalyst is purified.

Preferred embodiments of the present invention includes (but not limited to) the following items:

1. A method of regeneration of a spent sulfuric acid catalyst from alkylation of olefins and alkanes, said spent sulfuric acid catalyst containing organic impurities and water, said method comprising introducing said spent sulfuric acid catalyst into an electrolysis reactor containing an anode and a cathode, introducing air or $O_2$-containing gas into said spent sulfuric acid catalyst, and supplying electricity to said anode and said cathode, wherein the improvement comprises said cathode being $O_2$-diffusion cathode, and said air or $O_2$-containing gas being introduced into said spent sulfuric acid catalyst through the $O_2$-diffusion cathode, so that oxygen, and water and protons in the spent sulfuric acid catalyst undergo reduction reactions at the $O_2$-diffusion cathode, forming oxidants of hydrogen peroxide and hydroxyl free radicals, and thus at least a portion of the organic impurities are decomposed via reactions with oxygen and the so-formed oxidants.

2. The method of Item 1 wherein no organic peroxide is added to said spent sulfuric add catalyst before or during said supply of electricity.

3. The method of Item 1, wherein said anode comprises a semiconductor photocatalyst, and a photo energy or light radiation having a wavelength of 10 to 2000 nm is applied to said anode.

4. The method of Item 3, wherein said semiconductor photocatalyst comprises a metal oxide semiconductor.

5. The method of Item 3, wherein said semiconductor photocatalyst comprises Ti—$TiO_2$, or $TiO_2$.

6. The method of Item 1, wherein said anode comprises platinum, iridium, lead, lead dioxide, $TiO_2$, modified $TiO_2$, or graphite.

7. The method of Item 1, wherein said $O_2$-diffusion cathode comprises porous lead, porous graphite, porous graphene, porous carbon, porous tantalum, or gas-diffusion carbon-polytetrafluoroethylene cathode.

8. The method of Item 1 wherein said spent sulfuric acid catalyst in the electrolysis reactor is maintained at a temperature of −10 to 250° C., and a pressure lower than 20 atms.

9. The method of Item 1 wherein said spent sulfuric acid catalyst in the electrolysis reactor is maintained at a temperature of about 70° C., and about 1 atm.

10. The method of Item 1 further comprising evaporating $H_2O$ from the spent sulfuric add catalyst during said supply of electricity.

11. The method of Item 1, wherein the spent sulfuric acid catalyst introduced into the electrolysis reactor has a concentration of 90-97 wt % of sulfuric acid, and a regenerated sulfuric acid catalyst after a period of time of said electricity supplying has a concentration of 91-98 wt % of sulfuric acid.

12. An integrated process for regenerating a spent sulfuric acid catalyst from an alkylation unit and recycling the regenerated sulfuric acid as a catalyst to the alkylation unit, comprising carrying out a method of regeneration of a spent sulfuric acid catalyst as set forth in Item 1; withdrawing a regenerated sulfuric acid catalyst from the electrolysis reactor after a period of time of said electricity supplying; and recycling the regenerated sulfuric acid catalyst to the alkylation unit.

DETAILED DESCRIPTION OF THE INVENTION

Figure 1:
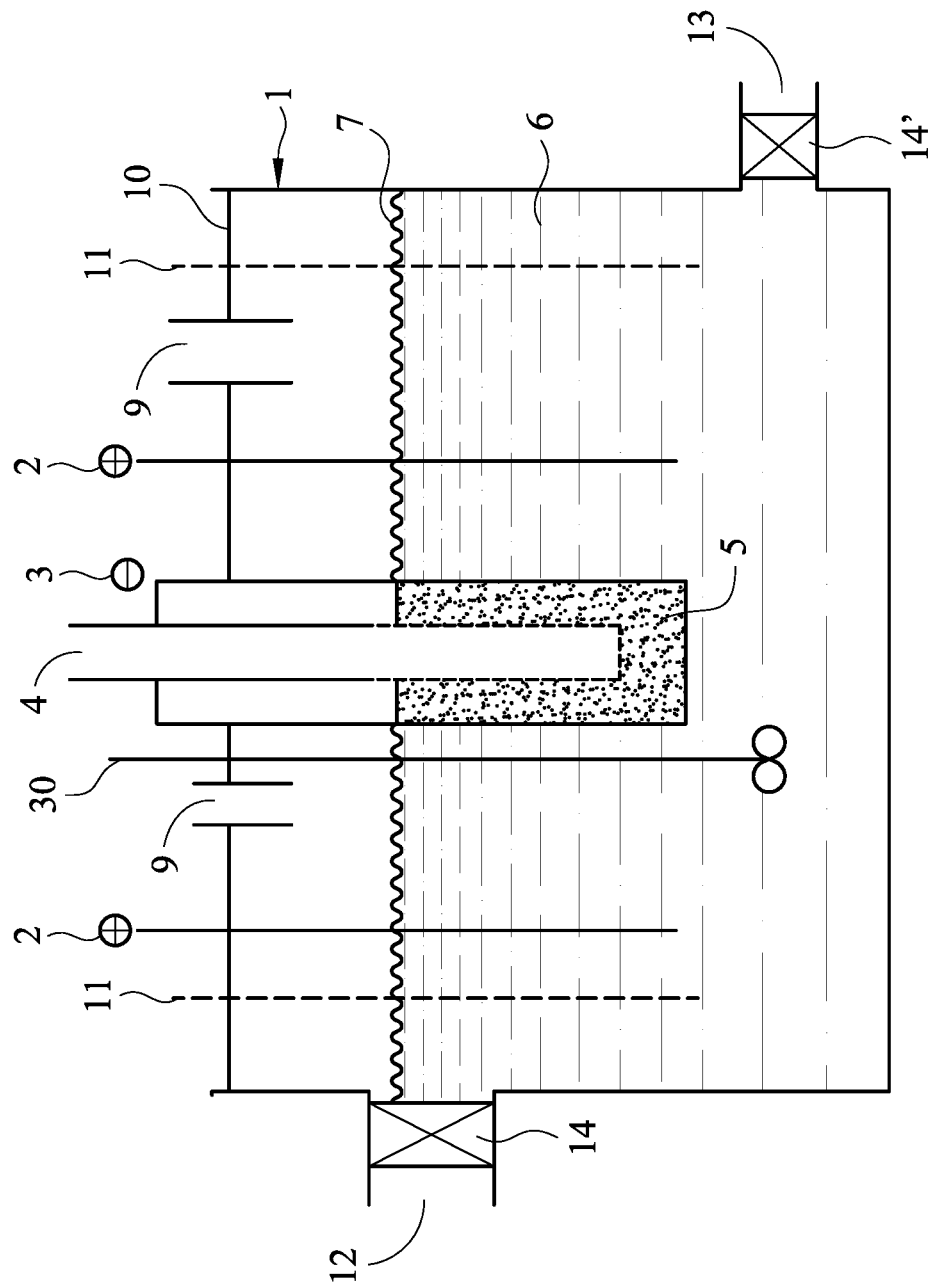
FIG. 1 is a schematic structure of semibatch tank reactor and of continuous stirred tank reactor (CSTR) spent sulfuric acid catalyst regeneration cell of the paired oxidation process for the integrated alkylation process using in situ regenerated sulfuric acid as catalyst.

The organic impurities to be removed from the spent sulfuric acid catalyst via this invention are various hydrocarbons, and conjunct polymers. These organic impurities contain small hydrocarbon compounds to possible large molecules such as conjunct polymer, which are also named red oil. These organic impurities are typically associated with the alkylation of olefins and alkanes, and are well known to one of ordinary skill in the art. Due to the complexity of organic hydrocarbon impurities in spent sulfuric acid catalyst from such alkylation process, it is very difficult to identify the composition of the organic impurities. Moreover, one of ordinary skill in the art would understand that the composition of the organic impurities depends upon the operating conditions of the alkylation process.

This invention also relates to an integrated process wherein the sulfuric acid regenerated in-situ is recycled to the alkylation process as a catalyst, i.e. integrating the alkylation process unit and the sulfuric acid regeneration unit as described in our prior U.S. Pat. No. 5,888,920.

While not wishing to be bound by theory, it is contemplated that the following reactions (1) to (35a) take place in the regeneration of sulfuric acid from the spent sulfuric acid catalyst of the alkylation of C3-C5 olefins and alkanes.

In this invention, a paired oxidation process for the regeneration of the spent sulfuric acid catalyst is carried out under mild operating conditions, less than 20 atms and in the temperature range from −50 to 250° C. The inlet oxidant is oxygen only, such as the oxygen in air or an oxygen-containing gas. The inlet oxidant is very hydrophobic reagent and is very difficult to dissolve in water. However, the inlet oxidant dissolves significantly in the spent sulfuric acid catalyst, which contains some hydrophobic organic impurities. The inlet air or oxygen-containing gas through the $O_2$-diffusion cathode will be reduced to hydrogen peroxide on the surface of cathode which provides electrons. Protons and water are provided by the spent sulfuric acid catalyst. The persulfate anion, $S_2O_8^{2-}$, also is reduced by cathode. The persulfate anion is generated by the anodic oxidation of sulfate anion on the surface of the anode. The generated persulfate anion mass transfer from the anode surrounding to the cathode in the bulk spent sulfuric acid. On the surface of the cathode, adsorbed hydroxyl free radical, $OH._{ads}$, hydroxyl free radical and sulfate anion free radical are also formed as indicated in reaction steps (1), (1a) and (1b), $$2H^+ + O_2 + 2e^- \rightarrow H_2O_2 \text{ or } 2OH._{ads} \text{ or } 2OH. \tag{1}$$

$$2H_2O + O_2 + 2e^- \rightarrow H_2O_2 + 2OH^- \text{ or } 2OH._{ads} + 2OH^- \text{ or } 2OH. + 2OH^- \tag{1a}$$

$$S_2O_8^{2-} + e^- \rightarrow SO_4^{2-} + SO_4^-. \tag{1b}$$

The anodic reactions of the electrolysis of spent sulfuric acid form persulfate anions, which then react with water to form hydrogen peroxide as shown in reaction steps (2) and (3):

$$2SO_4^{2-} \longrightarrow S_2O_8^{2-} + 2e^- \tag{2}$$

$$S_2O_8^{2-} + 2H_2O \longrightarrow 2HSO_4^- + H_2O_2 \tag{3}$$

$$S_2O_8^{2-} \xrightarrow{\text{phonon}} 2SO_4^-. \tag{3a}$$

The oxygen source to produce hydrogen peroxide in reaction step (3) is from persulfate anion and water. The thermal activation (usually temperature >45° C.) of persulfate anions generates two sulfate anion free radicals as shown in reaction step (3a). The anodically generated persulfate anion reacts with adsorbed hydroxyl free radical or hydroxyl free radical to produce sulfate anion free radical as indicated in reaction step (3b)

$$S_2O_8^{2-} + OH. \rightarrow SO_4^{2-} + SO_4^-. + \tfrac{1}{2}O_2 + H^+ \tag{3b}$$

The generated sulfate anion free radical reacts with water and hydroxyl anion in the bulk solution of the spent sulfuric acid catalyst to generate hydroxyl free radical as indicated in reaction steps (3c) and (3d), respectively.

$$SO_4^-. + H_2O \rightarrow SO_4^{2-} + OH. + H^+ \tag{3c}$$

$$SO_4^-. + OH^- \rightarrow SO_4^{2-} + OH. \tag{3d}$$

The anodic oxidation of water in the spent sulfuric acid also takes place, $$H_2O \rightarrow H^+ + OH._{ads} \text{ or } OH. + e^- \tag{4}$$

$$2H_2O \rightarrow 4H^+ + O_2 + 4e^- \tag{5}$$

The $OH_{ads}^•$ on the surfaces of both the anode and cathode can directly react with the hydrocarbon compounds of the organic impurities of the spent sulfuric acid. The $OH._{ads}$ free radicals desorbed from the surfaces of both the anode and cathode form hydroxyl free radicals, OH., which will diffuse into the bulk spent sulfuric add catalyst, where they react with the conjunct polymer, and hydrocarbons in the organic impurities of the spent sulfuric acid catalyst. The electrons generated by reaction steps (2), (4) and (5) on the surface of anode pass through an external wire connector and a power supplier to the cathode to carry out reaction steps (1), (1b) and (1c).

If the anode material is semiconductor such as $TiO_2$, the anodic reactions of the spent sulfuric acid catalyst by light radiation, i.e. photolysis or photoelectrolysis are $$2SO_4^{2-} \xrightarrow{h\nu} S_2O_8^{2-} + 2e^- \tag{2a}$$

$$S_2O_8^{2-} \xrightarrow{h\nu} 2SO_4^-. \tag{2b}$$

The photo formation of free radical oxidant as indicated in reaction step (2b) are two sulfate anion free radicals, $SO_4^-.$, from one persulfate anion, $S_2O_8^{2-}$. The photons provide energy, $E=h\nu$, to excite the electrons of the anodic semiconductor from valence band to conduction band and generate holes in valence band, where sulfate anions are oxidized as shown in the reaction step (2a). The formed persulfate anions can be generated by both electric energy as indicated in reaction step (2) and photo energy as indicated by reaction step (2a). The formed persulfate anions can decompose into two sulfate anion free radicals by both photon and phonon as indicated in reaction step (2b) and (3a). The formed persulfate anions also react with water to produce hydrogen peroxide as indicated in reaction step (3). The anodic oxidation of water also take place by using photo as the driving force instead of using electron as the driving force, $$H_2O \xrightarrow{h\nu} H^+ + OH_{ads}\cdot \text{ or } OH\cdot + e^- \quad (4a)$$

$$2H_2O \xrightarrow{h\nu} 4H^+ + O_2 + 4e^- \quad (5a)$$

The photolysis or photoelectrolysis reaction steps (2a), (2b), (4a) and (5a) can be promoted or enhanced by applying an electric field but no current is detected in the dark, meaning the driving energy is photon.

Both the anode and the cathode can generate adsorbed hydroxyl free radical. $OH._{ads}$, hydroxyl free radical, $OH.$, sulfate anion free radical, hydrogen peroxide and persulfate anion in the presence of air or oxygen in the spent sulfuric acid catalyst, we call this method paired oxidation process in this invention. Free radical, persulfate anion and hydrogen peroxide are very strong oxidants to oxidize hydrocarbon compounds and conjunct polymer. The decomposition of hydrogen peroxide has been described in our prior U.S. Pat. No. 5,547,655 as follows:

$$H_2O_2 \rightarrow H_2O + O \quad (6)$$

$$H_2O_2 \rightarrow 2OH. \quad (7)$$

$$H_2O_2 \rightarrow H. + HO_2. \quad (8)$$

The oxygen atom, hydroxyl free radical, perhydroxyl free radical, $HO_2\cdot$, sulfate anion free radical, $SO_4^-.$, adsorbed hydroxyl free radical, $OH._{ads}$, on the surfaces of both the anode and cathode, persulfate anion and hydrogen peroxide are active species will oxidize the organic impurities in the presence of air or oxygen.

Hydrogen peroxide is an environment friendly oxidant which can oxidize the organic impurities, i.e. red oil (conjunct polymer) in spent sulfuric acid from the alkylation process of the olefins and alkanes efficiently and economically in this invention. The standard reduction potentials of $H_2O_2$ imply that it is a strong oxidant in both the acidic (1.77 V v.s. NHE) and basic (0.87V v.s. NHE) solutions $$H_2O_2 + 2H^+ + 2e^- \rightarrow 2H_2O \quad E°=1.77V \quad (9)$$

$$HO_2^- + H_2O + 2e^- \rightarrow 3OH^- \quad E°=0.87V \quad (10)$$

Hydrogen peroxide oxidizes many kinds of organic species of red oil in the spent sulfuric add catalyst directly. The oxidation potential of hydroxyl free radicals has been estimated as +2.8 and +2V v.s. NHE at pH 0 and pH 14, respectively. The high reactivity of OH. free radical ensures that it will attack a wide range of organic compounds. The reactions friendly form $CO_2$ and water under aerobic condition in the spent sulfuric acid catalyst. The rate of generating free radicals, OH. and $HO_2.$, from $H_2O_2$ increases with a higher temperature, a higher $H_2O_2$ concentration and a lower pH value. In acidic solutions, hydrogen peroxide is one of the most powerful oxidizers known, and it is stronger than chlorine, chlorine dioxide and potassium permanganate. Also, through catalyst, light radiation and thermal energy or temperature, $H_2O_2$ can be converted into hydroxyl free radicals, OH., which are highly reactive as mentioned above. In the spent sulfuric acid catalyst, the sulfite anion ($SO_3^{2-}$) if it is present is oxidized by $H_2O_2$ to sulfate anion ($SO_4^{2-}$). The hydrogen peroxide in the presence of redox metallic cation, ferrous ion, for example, in the spent sulfuric acid catalyst generates the hydroxyl free radicals, which will then attack the organic impurities (red oil or conjunct polymer) in the spent sulfuric add catalyst. Equations of generation free radicals and the role of iron (II) catalyst, Fenton's reagent, are $$Fe^{2+} + H_2O_2 \rightarrow Fe^{3+} + OH^- + OH. \quad (11)$$

$$Fe^{3+} + H_2O_2 \rightarrow FeOOH^{2+} + H^+ \quad (12)$$

$$FeOOH^{2+} \rightarrow Fe^{2+} + HO_2. \quad (13)$$

The persulfate anion generated by both electrolysis and photolysis or photoelectrolysis in this invention is one of the strongest oxidants to oxidize the organic impurities. The standard redox potential for reaction step (2) is 2.1V v.s. NHE as compared to 1.77V v.s. NHE for that of hydrogen peroxide in acidic solution. In the presence of some catalyst or driving energy, such as photo radiation, heat, i.e. temperature from room temperature to 100° C. or higher, persulfate anion decomposes to form sulfate anion free radical, $SO_4^-.$, as indicated in reactions step (2b) and (3a). The persulfate anion is reduced on the surface of the cathode to generate sulfate anion free radical, $SO_4^-.$, as indicated in reaction step (1b). The persulfate anion also reacts with hydroxyl free radical to generate sulfate anion free radical as indicated in reaction step (3b). The sulfate anion free radical has a reaction mechanism similar to that of the hydroxyl free radical generated by the paired oxidation process of this invention. The sulfate anion free radical is one of the strongest oxidizing species with a redox potential 2.6V vs. NHE, which is similar to that of the hydroxyl free radical 2.7V vs. NHE. The sulfate anion free radical is more stable than that of the hydroxyl free radical and therefore is able to be transported to a greater distance in the bulk spent sulfuric acid catalyst, so that it can diffuse to the cathode or anywhere in the bulk solution. The high reactivity and high stability free radical gives this regeneration system advantages. The generation of sulfate anion free radical can significantly enhance the kinetic of persulfate oxidation of the organic impurities in the spent sulfuric acid catalyst. Some catalysts or driving force, such as transition metals, heat, photo radiation and the electrons from cathode, are found to be able to initiate generation of sulfate anion free radicals as indicated in the reaction steps (3a), (3b), (2b) and (1b). The heat-activated persulfate anion has been demonstrated to be able to oxidize the organic compounds at mild operating conditions.

The different types of free radicals such as hydroxyl free radical, OH., sulfate anion free radical, $SO_4^-.$, and peroxyhydroxyl free radical, $HO_2.$, inorganic and organic free radicals, are very active species which can react with the organic impurities under very mild operating conditions. We use OH. free radical as an example to describe the chemical equations of the decomposition of the organic impurities in the presence of the generated free radicals by photons, phonons, electrons and holes, cathode and anode and the inlet oxygen, leading to the formation of $CO_2$ and water during the paired oxidation process of this invention, which are

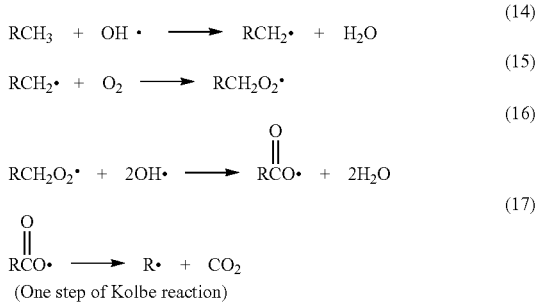

(14) $RCH_3 + OH\cdot \longrightarrow RCH_2\cdot + H_2O$

(15) $RCH_2\cdot + O_2 \longrightarrow RCH_2O_2\cdot$

(16) $RCH_2O_2\cdot + 2OH\cdot \longrightarrow R\overset{O}{\underset{\|}{C}}O\cdot + 2H_2O$

(17) $R\overset{O}{\underset{\|}{C}}O\cdot \longrightarrow R\cdot + CO_2$
(One step of Kolbe reaction)

where $RCH_3$ can be any species of the composition of olefins, alkanes, alkylates, conjunct polymer, and alkyl sulfate, such as 2,2,4-trimethylpentane, $C_8CH_{18}$, $(CH_3)_3CCH_2C(CH_3)_2CH_2C(CH_3)_2CH_2C(CH_3)_2CH_2C$ $(CH_3)_2CH_2CH(CH_3)_2$, i.e. conjunct polymer $C_{24}H_{50}$, and dialkyl sulfate, $(C_8H_{17})_2SO_4$, and etc. The chain reactions of reaction steps (14) to (17) go on until the red oil or conjunct polymer molecules are completely oxidized into $CO_2$ and $H_2O$ at very mild condition, because the reaction activation energies of free radical reactions, steps (14) to (16) and one step of Kolbe reaction, step (17), are very small. Accordingly, the oxidation chain reactions or propagation chain reactions, steps (14) to (17) can take place fast at low temperature or mild temperature said 50° C. or higher.

Now we use sulfate anion free radical as the oxidant, which abstracts hydrogen atom from the molecule of organic impurities to form hydrosulfate anion, i.e.

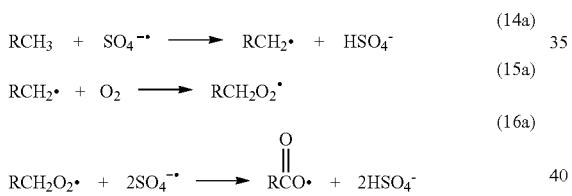

(14a) $RCH_3 + SO_4^{-\cdot} \longrightarrow RCH_2\cdot + HSO_4^-$ (15a) $RCH_2\cdot + O_2 \longrightarrow RCH_2O_2\cdot$ (16a) $RCH_2O_2\cdot + 2SO_4^{-\cdot} \longrightarrow R\overset{O}{\underset{\|}{C}}O\cdot + 2HSO_4^-$ The RCOO. then proceed the one step of Kolbe reaction as indicated in the reaction step (17).

The peroxyhydroxy free radical, $HO_2\cdot$, also plays a role in the propagation chain reactions as indicated in reaction steps (18) to (21). The generated $RCH_2O_2\cdot$ free radical by reaction step (21) and $RCH_2\cdot$ free radical by reaction step (18) can proceed reaction steps (14) to (17) to produce $CO_2$ and $H_2O$, resulting the removal of organic impurities in the spent sulfuric acid catalyst. The reactions of $RCH_3$ and $HO_2\cdot$ free radicals in the presence of $OH\cdot$ free radicals and inlet oxygen are the reaction steps (14) to (21).

(18) $RCH_2\cdot + HO_2\cdot \rightarrow RCH_2O\cdot + OH\cdot$ (18a) $H\cdot + O_2 \rightarrow HO_2\cdot$

(19) $RCH_2O_2\cdot + RCH_3 \rightarrow RCH_2O_2H + RCH_2\cdot$

(20) $RCH_2O_2H \rightarrow RCH_2O\cdot + OH\cdot$

(21) $RCHO\cdot + HO_2\cdot \rightarrow RCH_2O\cdot + OH\cdot$

The metallic cation also can play a role in the oxidation of organic impurities as catalyst, for example, the redox Fe (II) and Fe (III) redox cations, which play the roles of oxidations in the spent sulfuric acid catalyst as indicated in the reaction steps (22) to (25) as follows:

(22) $RCH_2\cdot + Fe^{3+} \rightarrow RCH_2^+ + Fe^{2+}$

(23) $RCH_2^+ + H_2O \rightarrow RCH_2OH + H^+$

(24) $RCH_2O_2\cdot + Fe^{2+} \rightarrow RCH_2O_2^- + Fe^{3+}$

(25) $RCH_2O_2^- + OH\cdot \rightarrow RCH_2O_2\cdot + OH^-$ where the organic free radical, $RCH_2O_2\cdot$, is available from reaction steps (15), (21) and (25). Based on reaction steps (16) and (17), $RCH_2O_2\cdot$ free radicals react with hydroxyl free radicals to produce $CO_2$ and $H_2O$ as shown in reaction steps (16) and (17), resulting the removal of organic impurities in the spent sulfuric acid catalyst.

In addition to organic free radicals, organic peroxides, inorganic peroxides, inorganic free radicals, and redox mediators or ions, some oxygenates are possibly formed during the paired oxidation process in this invention. It does not affect the regeneration of the spent sulfuric acid catalyst by the paired oxidation process of this invention. Examples are provided as following:

(1) If the oxygenate is oxalic acid,

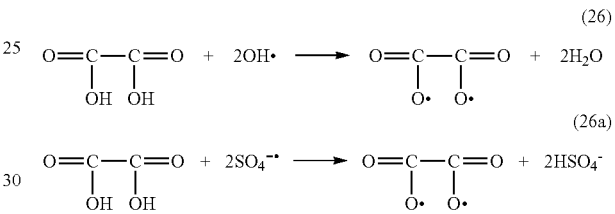

(26)

(26a)

One step of Kolbe reaction,

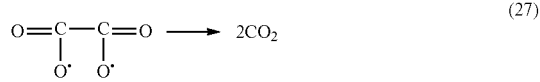

(27)

(2) If the oxygenate is maleic acid,

(28) $HOOCHC=CHCOOH + 2OH\cdot \rightarrow \cdot OOCH=CHCOO\cdot + 2H_2O$ (28a) $HOOCHC=CHCOOH + 2SO_4^{-\cdot} \rightarrow \cdot OOCH=CHCOO\cdot + 2HSO_4^-$ One step of Kolbe reaction,

(29) $\cdot OOCHC=CHCOO\cdot \rightarrow H\dot{C}=\dot{C}H + 2CO_2$

(30) $H\dot{C}=\dot{C}H + 2O_2 \rightarrow \cdot O-OCH=CHO-O\cdot$

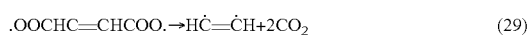

(31)

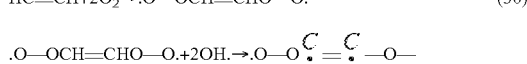

(31a)

The oxygen end site free radicals shift and rearrange to the carbon atom to form C—O. bond,

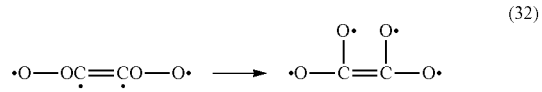

(32)

breaking of π bond and providing electron to form the two C=O double bond,

 (33)

One step of Kolbe reaction,

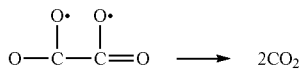 (34)

The HĊ=ĊH free radical is possible to form propylene, HC≡HC, molecule. The .O—O—Ċ=Ċ—O—O. free radical is possible to form .O—O—C≡C—O—O. free radical, which rearranges to

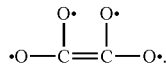

The

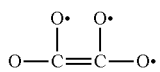

free radical is possible to form

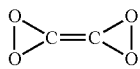

molecule and

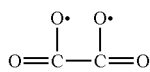

free radical. The

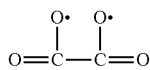

free radical is also possible to form

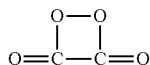

molecule. These dual free radical sites couple reaction to form stable molecular triple bond or cyclic ring molecules, which make the oxidation rate of maleic acid to $CO_2$ and $H_2O$ be slow. Because the propylene molecule and these cyclic compounds are small molecules which are, in general, low boil point molecules, they can easily evaporate from the spent sulfuric acid. If the OH. and $SO_4^-$. free radicals concentration are high and the mild operating temperature is not too low, said 50° C. or more, the maleic acid intermediate can be mainly oxidized into $CO_2$ and $H_2O$. The overall reaction of maleic acid oxidation to produce $CO_2$ and water in the spent sulfuric acid by the paired oxidation process in this invention is

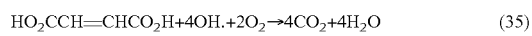 (35)

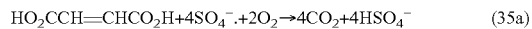 (35a)

Based on the above reaction steps (1) to (35a), the organic impurities in the spent sulfuric add catalyst can be removed at very mild operating conditions by the paired oxidation process in this invention. The reaction steps (1) to (35a) and more reaction steps which are not indicated in this invention will take place in the bulk spent sulfuric acid catalyst as well as on the surfaces of both the cathode and the anode.

The paired oxidation process includes two types of reactions which occur in and on three locations of the regeneration unit. Type 1 is homogeneous reactions which occur in the bulk solution of the spent sulfuric acid catalyst. Type 2 is heterogeneous reactions which occur in two locations. One is on the surface of the anode and the other one is on the surface of the cathode, where the free radicals such as hydroxyl free radicals become an adsorbed form. The organic impurities species diffuse to the surfaces of the anode and the cathode, and then proceed the related reaction steps, for example, such as reaction steps (14) to (17), where the hydroxyl free radical, OH., changes to adsorbed hydroxyl free radical, $OH._{ads}$, in the reaction equations.

As describe in the above reactions, the paired oxidation process proceeds under mild operating conditions, less than 20 atms and in the temperature range from −50 to 250° C. Reaction steps (1) to (35a) are the reactions known by the inventors so far, there may be more reactions taking place in the paired oxidation process in this invention. Accordingly, many types of active species generated in the paired oxidation process in this invention include (1) the organic free radicals, (2) the inorganic free radicals, (3) the organic and inorganic peroxides, (4) redox reagents or ions, and compounds. All of the generated active species or intermediates enhance the paired oxidation process to remove the organic impurities and water, resulting high purity and concentration of the regeneration sulfuric acid.

The composition and concentration of a homogenous catalyst are the standard to judge the activity of the homogeneous catalyst, and the activity of spent sulfuric acid treated by the paired oxidation process in this invention is similar to the fresh catalyst by comparing the experimental results with the data raised by L F. Albright et al "Alkylation of isobutane with olefins yields of alkylates for different olefins" I&EC, 32(1993), pp 2991-2996. And D. J. AmEnde et al, "Effect of sulfuric acid composition on the kinetics and mechanism of sulfuric acid catalyzed alkylations of isobutane with alkenes" in Symposium on Alkylation, Aromatization, Oligomerization of Short Chain Hydrocarbons over Heterogeneous Catalysts, New York, Aug. 25-30 (1991).

In addition to the advantages in comparison with the traditionally commercialized process as discussed in U.S. Pat. No. 5,547,655, the present invention further improves the method disclosed in U.S. Pat. No. 5,547,655. In the present invention, the sources of oxidants are the inlet air or oxygen-containing gas, and water in the spent sulfuric acid catalyst. The paired oxidation process of the present invention converts the sulfate anion into persulfate anion, which forms sulfate anion free radicals; and converts persulfate anion and water into hydrogen peroxide as well as converting oxygen and water into hydrogen peroxide, adsorbed hydroxyl free radicals, hydroxyl free radicals and peroxyhydroxyl free radicals, all of which proceed the oxidation of organic impurities in the spent sulfuric acid catalyst as indicated in the reaction steps (1) to (35a). As a result, the removal of organic impurities and regeneration of spent sulfuric acid can be carried out under more mild operating conditions with a faster rate. This invention can be widely applied to the treatment of any waste liquid or aqueous solution containing organic impurities.

A semibatch tank reactor 1 for use in the regeneration of the spent sulfuric acid catalyst according to the present invention is shown in FIG. 1. A continuous stirred tank reactor (CSTR) also has the same structure, but the operating types and performance thereof are different. Air, as an oxidant, is continuously supplied via an air inlet 4 to a gas-diffusion or $O_2$-diffusion cathode 3 during the operation. The spent sulfuric acid catalyst is charged into the semibatch tank reactor 1 via an inlet 12. The regenerated spent sulfuric acid catalyst is discharged from the semibatch tank reactor 1 via an outlet 13. The operations are batchwise, wherein the spent sulfuric acid catalyst is charged into the semibatch tank reactor 1 by opening a valve 14, and is discharged after a period of operation time via another valve 14'. The charging and discharging will become continuous, if the semibatch tank reactor 1 is operated as a CSTR reactor.

Since the semibatch tank reactor 1 is operated batchwise and the alkylation unit is continuously operated, two storage tanks (not shown) are provided, one of which is for storing the spent sulfuric acid catalyst, and the other of which is for storing the regenerated sulfuric add, in order to integrate the semibatch tank reactor 1 into the alkylation unit.

Anode 2 which can be constructed one anode 2 or two anodes 2 at front side and back side of a gas-diffusion cathode 3. The anode materials are platinum, iridium, lead, lead dioxide, $TiO_2$, modified $TiO_2$, DSA®, graphite etc. The gas-diffusion or $O_2$-diffusion cathode 3 is a nanoporous or microporous electrical conductive material in a cylindrical shape or a different design shape with air inlet 4 through its center. The materials for gas-diffusion cathode 3 are porous lead, porous graphite, porous graphene, porous carbon, and porous tantalum, etc. Carbon is preferred, such as reticulated vitreous carbon and carbon-felt. Many other gas-diffusion cathodes are also satisfactory cathode, such as gas-diffusion carbon-PTFE cathode (PTFE, polytetrafluoroethylene). The air or oxygen oxidant of the paired oxidation process in this invention is flowing into the gas-diffusion cathode 3 via line 4. The air is pumped by an air pump (not shown) from atmosphere through the air inlet 4 which is tightly sealed on or into the gas-diffusion cathode 3. The outside of the diffusion zone which is higher than the liquid level 7 of the spent sulfuric acid catalyst 6 is sealed tightly to prevent a leakage of pumping air into atmosphere. Air bubbles 5 which disperse into the bulk spent sulfuric acid catalyst 6 are formed by pumping air through the porous gas-diffusion cathode 3. Both the air bubbles 5 and the produced $CO_2$ gas play an important role of mixing the bulk spent sulfuric acid catalyst 6 in the reactor with/without a mixer 30. The amount of the spent sulfuric acid catalyst 6 containing partially regenerated or fully regenerated spent sulfuric acid in the semibatch tank reactor 1 or CSTR reactor is controlled by measuring the liquid level 7 of the spent sulfuric acid catalyst 6. The mixer 30 if it is required is fixed and operates at the center of semibatch tank reactor and CSTR reactor regeneration cell. The unreacted air, the produced $CO_2$ gas and $H_2O$ vapor flow out into an absorber (not shown) via gas outlets 9. The semibatch tank reactor 1 is provided with an air-tight cover 10. Two UV light or any other suitable light or photo radiation sources 11 are fixed in parallel with the anodes 2 if required. The inlet 12 of the spent sulfuric acid catalyst is fixed at a position higher or lower than the liquid level 7 of the spent sulfuric acid catalyst 6 in the reactor, and the outlet 13 of regenerated sulfuric acid is fixed on a sidewall and near the bottom position of the reactor 1. The flow rates at the inlet 12 and the outlet 13 are controlled by valves 14 and 14', respectively. The spent sulfuric acid catalyst is withdrawn from the storage tank to the inlet 12, which store the spent sulfuric acid catalyst from the alkylation unit. The regenerated sulfuric acid discharged from the outlet 13 is stored in the storage tank, and then is recycled to the alkylation unit, or is directly recycled to the alkylation unit for the CSTR operation.

It is apparent to people ordinarily skilled in the art that more than one of the semibatch tank reactor 1 can be used in series, or a portion of the regenerated sulfuric acid discharged from the outlet 13 can be recycled back to the inlet 12, to achieve a higher purity of the regenerated sulfuric acid.

Figure 2:
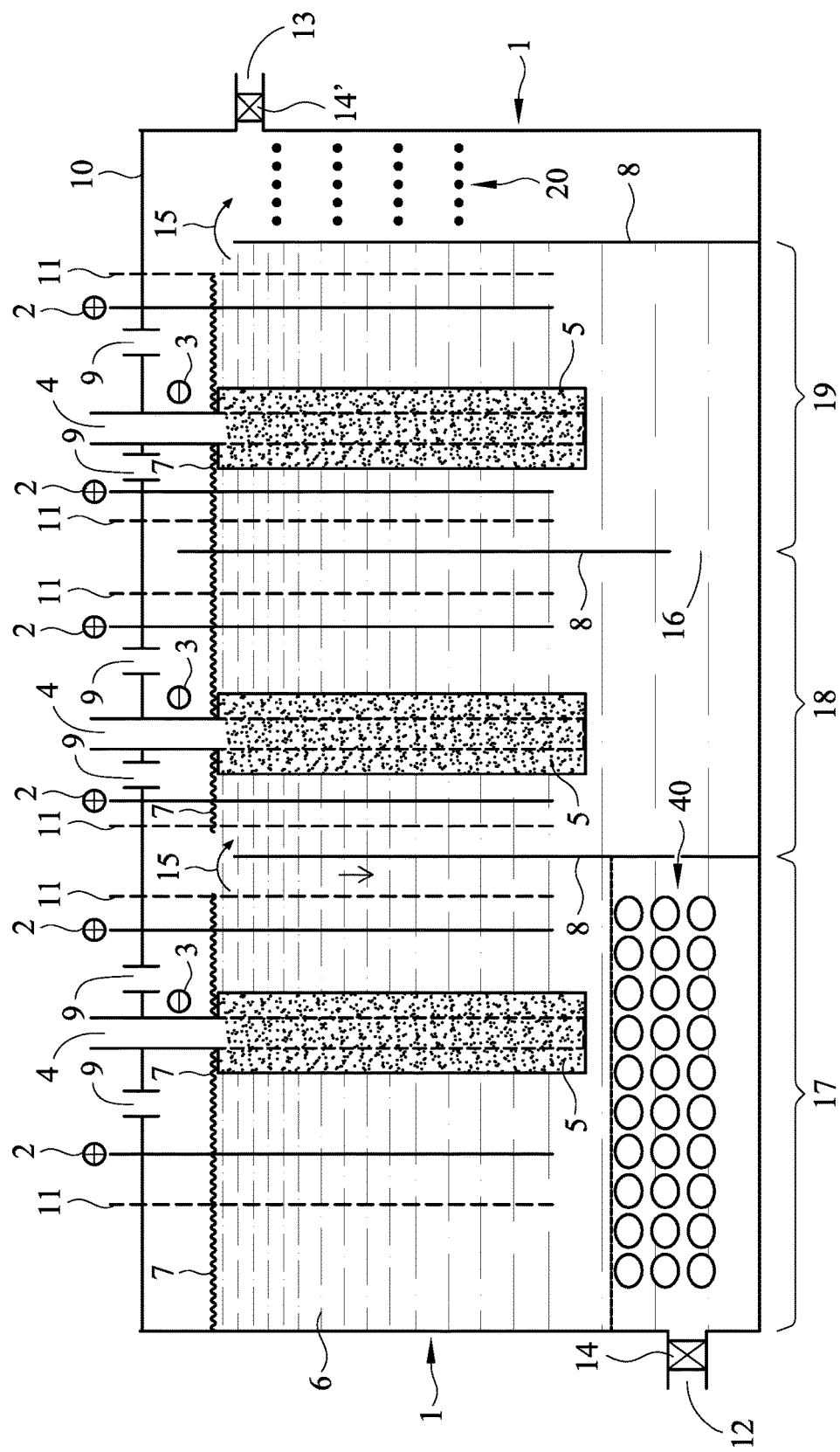
FIG. 2 is a schematic structure of plug flow reactor (PFR) rectangular tunnel frame of spent sulfuric acid catalyst regeneration cell of the paired oxidation process for the integrated alkylation process using in situ regenerated sulfuric acid as catalyst.

FIG. 2 shows a schematic structure of a plug flow reactor 1 (PFR) for regenerating the spent sulfuric acid catalyst by the paired oxidation process of the present invention. A plug flow reactor sometimes is called a continuous tubular or tunnel reactor, where chemical reactions take place in a continuously flowing system of a plurality of chambers formed by dividing the reactor with barrier plates. The spent sulfuric acid catalyst is introduced into the first chamber, then flowing from the first chamber to the second chamber, and so on, until it is discharged from the last chamber. In each chamber the anode, gas-diffusion cathode, light or photo radiation sources are installed similarly as in the reactor 1 shown in FIG. 1, wherein like elements/parts are designated by like numerals. Barrier plates 8 are installed in the PFR reactor 1 to divide it into different regeneration chambers 17, 18, 19, 20 and so on in series, if necessary. A flow distributor 40 is provided in the first chamber 17 to keep uniform flow distribution of the spent sulfuric acid catalyst introduced via the inlet 12 and valve 14. The spent sulfuric acid catalyst 6 is regenerated in sequence in the chambers with an overflow 15 over the top of the barrier plate 8 and an underflow through a gap or holes 16 at the bottom of the barrier plate 8. If the electrodes and light or photo radiation devices can be installed in parallel to the flow direction of the PFR reactor, no barrier plate is required and thus no chamber 17, 18, 19, and 20. On the other hand, if the electrodes, and light or photo radiation devices are fixed perpendicularly to the flow direction of the spent sulfuric acid catalyst and partially regenerated spent sulfuric acid catalyst, the barrier plates are used to form many subunits as described above.

The reactor design mentioned above in this invention includes (but not limited to) three types: semibatch, CSTR and PFR reactors, other types of reactors are also applicable.

The mixing or agitation of the spent sulfuric acid catalyst is good even in the absence of a mixer, because the inlet air, the products of the paired oxidation process in this invention such as $CO_2$, $H_2O$ and small hydrocarbon molecules or oxygenated compounds are gas phase and give a very good bubble mixing effect during the paired oxidation process in this invention as shown in the reactions of steps (1) to (35a), and especially, at the operating temperature in the favor range from −10 to 100° C. and the operating pressure at one atmosphere pressure or lower.

The paired oxidation process of the present invention regenerates the spent sulfuric acid catalyst in-situ, and thus it provides the almost fresh sulfuric acid which can be recycled to the alkylation unit as the catalyst. That means the method of the present invention can be easily integrated with the alkylation process as reported or claimed in our prior patent U.S. Pat. No. 5,888,920.

EXAMPLE 1

100 ml of a spent sulfuric acid catalyst was introduced into the semibatch reactor as shown in FIG. 1, but there was no photo radiation source 11. Platinum net was chosen as anode and $O_2$-diffusion carbon-PTFE was chosen as cathode. The specific gravity of the spent sulfuric acid catalyst was 1.84 and its color was dark-black. The spent sulfuric acid catalyst was heated to maintain the temperature thereof at 70° C., and then air was introduced into the spent sulfuric acid catalyst through the $O_2$-diffusion carbon-PTFE cathode. Electric energy was applied to the reactor at 7.0 volts. Active free radicals and oxidants were generated by the paired oxidation process, and the organic impurities in the spent sulfuric acid catalyst were converted to $CO_2$, $H_2O$ and small molecular compounds as described above. At temperature 70° C., water and small molecular compounds will evaporate gradually. Adjusting the operating parameters such as the electricity charge amount, the inlet air flow rate, the temperature and heating time, we can control the percentages of the residue organic impurities and water, respectively, in the regenerated sulfuric add.

After the paired oxidation process, organic impurities and water can be removed simultaneously. Finally, the COD and water content of the spent sulfuric acid catalyst were reduced from 236000 to 4500 and from 4.0 wt % to 0.5 wt %, respectively. The dark-black color of the spent sulfuric acid catalyst was changed to light-yellow.

EXAMPLE 2

100 ml of a spent sulfuric acid catalyst was introduced into a semibatch reactor as shown in FIG. 1. The setup was similar to Example 1 except Ti—$TiO_2$ screen was chosen to replace platinum as the anode. Electric potential was applied to the reactor at 2.0 volts. At this apply potential almost no current was observed, resulting no electric energy was applied to the reaction system. After photo radiation energy being applied to the Ti—$TiO_2$ screen anode with a wavelength of 253 nm, a significant electric current was observed. In this situation, hydrogen peroxide, free radicals and many active intermediates were generated, and the organic impurities in the spent sulfuric acid catalyst were converted to $CO_2$, $H_2O$ and small molecular compounds as described above. At temperature 70° C., water and small molecular compounds will evaporate gradually. Finally, the COD and water content of the spent sulfuric acid catalyst were reduced from 236000 to 5100 and from 4.0 wt % to 0.8 wt %, respectively. The color of the spent sulfuric acid catalyst was changed from dark-black to light-yellow.

The invention claimed is:

1. A method of regeneration of a spent sulfuric acid catalyst from alkylation of olefins and alkanes, said spent sulfuric acid catalyst containing organic impurities and water, said method comprising:
   introducing said spent sulfuric acid catalyst into an electrolysis reactor containing an anode and a cathode,
   introducing air or $O_2$-containing gas into said spent sulfuric acid catalyst, and
   supplying electricity to said anode and said cathode,
   wherein said cathode is an $O_2$-diffusion cathode which is selected from porous lead, pore graphene, and gas-diffusion carbon-polytetrafluroroethylene cathode, and said air or $O_2$-containing gas is introduced into said spent sulfuric acid catalyst through the $O_2$-diffusion cathode, so that oxygen, and water and protons in the spent sulfuric acid catalyst undergo reduction reactions at the $O_2$-diffusion cathode, forming oxidants of hydrogen peroxide and hydroxyl free radicals, and thus at least a portion of the organic impurities are decomposed via reactions with oxygen and the so-formed oxidants.

2. The method of claim 1 wherein no organic peroxide is added to said spent sulfuric acid catalyst before or during said supply of electricity.

3. The method of claim 1, wherein said anode comprises a semiconductor photocatalyst, and a photo energy or light radiation having a wavelength of 10 to 2000 nm is applied to said anode.

4. The method of claim 3, wherein said semiconductor photocatalyst comprises a metal oxide semiconductor.

5. The method of claim 3, wherein said semiconductor photocatalyst comprises Ti—$TiO_2$, or $TiO_2$.

6. The method of claim 1, wherein said anode comprises platinum, iridium, lead, lead dioxide, $TiO_2$, modified $TiO_2$, or graphite.

7. The method of claim 1 wherein said spent sulfuric acid catalyst in the electrolysis reactor is maintained at a temperature of −10 to 250° C., and a pressure lower than 20 atms.

8. The method of claim 1 wherein said spent sulfuric acid catalyst in the electrolysis reactor is maintained at a temperature of about 70° C., and about 1 atm.

9. The method of claim 1 further comprising evaporating $H_2O$ from the spent sulfuric acid catalyst during said supply of electricity.

10. The method of claim 1, wherein the spent sulfuric acid catalyst introduced into the electrolysis reactor has a concentration of 90-97 wt % of sulfuric acid, and a regenerated sulfuric acid catalyst after a period of time of said electricity supplying has a concentration of 91-98 wt % of sulfuric acid.

11. An integrated process for regenerating a spent sulfuric acid catalyst from an alkylation unit and recycling the regenerated sulfuric acid as a catalyst to the alkylation unit, comprising carrying out a method of regeneration of a spent sulfuric acid catalyst as set forth in claim 1; withdrawing a regenerated sulfuric acid catalyst from the electrolysis reactor after a period of time of said electricity supplying; and recycling the regenerated sulfuric acid catalyst to the alkylation unit.

* * * * *